United States Patent
Pai et al.

(10) Patent No.: US 10,350,296 B1
(45) Date of Patent: Jul. 16, 2019

(54) CHEWABLE GELATIN FORMULATIONS

(71) Applicant: Aspire Pharmaceuticals, Somerset, NJ (US)

(72) Inventors: Madhav Pai, Somerset, NJ (US); Ritesh Patel, Somerset, NJ (US)

(73) Assignee: Aspire Pharmaceuticals, Somerset, NJ (US)

( * ) Notice: Subject to any disclaimer, the term of this patent is extended or adjusted under 35 U.S.C. 154(b) by 0 days.

(21) Appl. No.: 14/338,311

(22) Filed: Jul. 22, 2014

Related U.S. Application Data (60) Provisional application No. 61/856,901, filed on Jul. 22, 2013.

(51) Int. Cl.

| | | |
|---|---|---|
| *A61K 35/12* | (2015.01) | |
| *A61K 35/60* | (2006.01) | |
| *A61K 35/35* | (2015.01) | |
| *A61K 35/32* | (2015.01) | |
| *A61K 36/00* | (2006.01) | |
| *A61K 47/42* | (2017.01) | |
| *A61K 9/00* | (2006.01) | |

(52) U.S. Cl.
CPC ............ *A61K 47/42* (2013.01); *A61K 9/0056* (2013.01)

(58) Field of Classification Search
None
See application file for complete search history.

(56) References Cited

U.S. PATENT DOCUMENTS

| | | |
|---|---|---|
| D201,228 S | 5/1965 | Horne |
| D283,931 S | 5/1986 | Baum |
| D375,549 S | 11/1996 | Sauer |
| D432,641 S | 10/2000 | Burrows |
| D433,750 S | 11/2000 | Burrows |
| D434,136 S | 11/2000 | Burrows |
| D437,407 S | 2/2001 | Burrows |
| D555,783 S | 11/2007 | Chen et al. |
| 7,662,406 B1 * | 2/2010 | Xie ............ A23L 1/0029 424/451 |
| D613,029 S | 4/2010 | Krumholz et al. |
| D671,636 S | 11/2012 | Nishino |
| RE44,459 E | 8/2013 | Kuczynski et al. |
| D726,899 S | 4/2015 | Pai et al. |
| 2012/0107395 A1 * | 5/2012 | Xie ............ A61K 35/741 424/452 |
| 2014/0112982 A1 * | 4/2014 | Cao ............ A23G 3/004 424/456 |

FOREIGN PATENT DOCUMENTS

WO  WO 2012167757 A1 * 12/2012 ............ A23G 3/004

OTHER PUBLICATIONS

Website document entitled "Cargill obtains approval for use of sunflower lecithin in food in Japan" (available at http://www.cargill.com/news/releases/2014/NA31654548.jsp). Downloaded from website Dec. 21, 2015.*

Website document entitled: "Lecithin (emulsifer)" (available at http://nouveauraw.com/thickeners-binders-emulsifiers/raw-lecithin-thickener). Downloaded from website Dec. 21, 2015.*

U.S. Appl. No. 29/461,325, filed Jul. 22, 2013, now U.S. Pat. No. D. 726,899.

* cited by examiner

*Primary Examiner* — Christopher R Tate
*Assistant Examiner* — Russell G Fiebig
(74) *Attorney, Agent, or Firm* — McCarter & English, LLP; Maneesh Gulati (57) ABSTRACT

Chewable gelatin formulations that include a bovine gelatin and a fish gelatin.

8 Claims, 5 Drawing Sheets

CHEWABLE GELATIN FORMULATIONS

The present application claims the benefit of U.S. Ser. No. 61/856,901, filed Jul. 22, 2013, and hereby incorporated by reference in its entirety.

BACKGROUND

A significant portion of the population cannot, or prefers not, to swallow medicaments or consumer health products whole. As an alternative, many consumers prefer to chew, rather than swallow, their dosage in the form of a chewable formulation. Chewable gelatin formulations can provide the consumer a chewable option for administering therapeutically active agents, i.e., agents that can be used to provide therapy, prophaylactically to prevent disease, or agents that otherwise promote good health.

There remains a need for chewable gelatin formulations that can be used to deliver therapeutically active agents that have an acceptable shelf life, and that possess a mouth feel favored by consumers.

BRIEF SUMMARY OF THE INVENTION

It has been found that chewable gelatin formulations can be provided with improved mouth feel by incorporating a bovine gelatin and a fish gelatin. Accordingly, one aspect of the present application provides chewable gelatin formulation that includes a bovine gelatin and a fish gelatin. The chewable gelatin formulation can encapsulate a therapeutically active agent, such as, but not limited to, vitamins, minerals, fish oil, essential oils, OTC active ingredients and herbal extracts that are believed, among other things, to promote good health.

In one embodiment, the weight ratio of bovine gelatin:fish gelatin is from about 0.5 to about 7.5, or from about 0.5 to about 5.0, or from about 1.0 to about 3.5. In one particular embodiment, the weight ratio of bovine gelatin:fish gelatin is about 2.9.

In one embodiment, the bovine gelatin has a bloom value of from about 125 to about 175 (e.g., about 150) and the fish gelatin has a bloom value of from about 250 to about 300 (e.g., about 275).

In one embodiment, the chewable gelatin formulation can further include at least one plasticizer (including, but not limited to, glycerin, maltitol and a polyethylene glycol (PEG)), at least one gel forming agent (e.g, food starch, a modified food starch, bovine collagen peptides and sodium starch glycolate), at least one anti-tacking and softening agent (e.g., sunflower lecithin, soy lecithin, hydrogenated vegetable oil, beeswax, coconut oil and palm oil), water, optionally, at least one flavorant (e.g., vanillin, lemon oil, citric acid, natural flavors, artificial flavors, essential oils, dairy flavors, and herbal extracts), optionally, at least one colorant (e.g., natural and artificial colorants) and a natural preservative (eg., citric acid, potassium sorbate, rosemary extract and alpha tocopherol). In one embodiment, the chewable gelatin formulation can further include a sweetener (e.g., xylitol, sucralose, aspartame, sucrose, glucose, high fructose corn syrup and stevia rabaudiana).

According to one non-limiting embodiment, the chewable gelatin formulation is prepared from a solution that includes (w/w) from about 15% to about 32% of bovine gelatin having a bloom value of from about 125 to about 175 (e.g., about 19%), from about 3.5% to about 13.0% of fish gelatin having a bloom value of from about 250 to about 300 (e.g., about 6.5%), from about 20.0% to about 35% of glycerin (e.g., about 27.1%), from about 20 to about 40% of water (e.g., about 30.3%); from about 2.0 to about 20.0% of a modified potato starch (e.g, about 13%), from about 6.0 to about 25.0% of bovine collagen peptides (e.g., about 10.0%), from about 0.2% to about 5.0% of sunflower lecithin (e.g. about 0.7%), from about 0.01% to about 100% of a flavorant selected from one or more of vanillin, lemon oil, citric acid and natural and artificial flavors, optionally, less than 2% of sucralose, optionally, less than 5% of a colorant and less than 2.0% of a natural preservative (e.g. about 1.25%). After drying, non-water component amounts of the chewable gelatin formulation can each increase by about 34%, and the water can be reduced by about 77%.

According to one non-limiting embodiment, a dried gelatin sheath is provided that includes from about 22% to about 34% of bovine gelatin having a bloom value of from about 125 to about 175, from about 4.5% to about 18.0% of fish gelatin having a bloom value of from about 250 to about 300, from about 26.0% to about 47% of glycerin, from about 4.0% to about 10.0% of water; from about 2.6% to about 28.5% of a modified potato starch, from about 7.8% to 35.0% of a bovine collagen peptide, from about 0.3% to about 7.0% of sunflower lecithin, from about 0.3% to about 5.0% a flavorant selected from one or more of vanillin, lemon oil, citric acid and natural and artificial flavors, optionally, less than 5.0% of sucralose; optionally, less than 5.0% of a colorant and less than 5% of a natural preservative. The dried chewable gelatin formulation can have an average hardness of −50-200 grams, as measured on a calibrated Texture Analyzer.

A second aspect of the present application provides a process for preparing a chewable gelatin formulation that includes preparing a first mixture comprising water and a gel forming agent(s), preparing a second mixture comprising a first plasticizer, maintaining water in a temperature controlled vessel at a temperature of about 55-70° C., transferring a second quantity of a second plasticizer to the temperature controlled vessel and allow said vessel to maintain the temperature of about 55-70° C., introducing a first gelatin and a second gelatin to the temperature controlled vessel, introducing the first mixture and the second mixture to the temperature controlled vessel to form a encapsulating mixture, deaerating the encapsulating mixture and allow the encapsulating mixture to attain a viscosity of about 5000-20,000 cps, preparing a fill mixture containing a therapeutically active agent, and introducing the encapsulating mixture and the fill mixture to a die roll encapulsation machine to encapsulate the fill mixture with the encapsulating mixture.

In one embodiment, the first gelatin is a bovine gelatin having a bloom value of from about 125 to about 175 and the second gelatin is a fish gelatin having a bloom value of from about 250 to about 300. In one embodiment, the first plasticizer and the second plasticizer are glycerin. In one embodiment, the gel forming agent is a modified potato starch or a combination of modified potato starch and bovine collagen peptides.

DETAILED DESCRIPTION OF THE INVENTION

Unless indicated otherwise, percentages refer to weight percent of the "shell" solution used to encapsulate a fill material, as initially applied to the encapsulating machine, and prior to any drying step. Formulation percentages provided herein do not include, or account for, components of the fill material that is to be encapsulated by the chewable gelatin formulations, and are thus based solely on the total weight of encapsulating solution components.

As used herein, the term "therapeutically active agent" is understood in the broadest sense generally accepted in the art to be a compound or compounds which are used to treat or prevent any disease or undesirable condition which afflicts an animal, or to a compound or compounds that are used prophylactically to prevent such disease or undesirable condition or to generally promote good health (e.g., vitamins and homeopathic agents).

As used herein, the term "bloom" refers to a value determined by measuring the weight in grams required to move a plunger 0.5 inch in diameter, 4 mm into a 6.67% gelatin gel that has been held for 17 hours at 10° C.

As used herein, the term "bovine gelatin" refers to gelatin derived from a bovine source, such as gelatin derived from cow bones, cow skin, cow tendons and/or cow tissues. In a preferred embodiment, the bovine gelatin is obtained only from cow bones.

As used herein, the term "fish gelatin" refers to a gelatin derived from a fish source. In a preferred embodiment, the fish gelatin is obtained from fish skin and/or fish scales.

As used herein, the term "low bloom gelatin" refers to a gelatin having a bloom count between 125-175 bloom.

As used herein, the term "high bloom gelatin" refers to a gelatin having a bloom count between 250-300 bloom.

As used herein, the term "gel forming agent" refers to any agent that aids in the formation of a gel and/or stablilization of a gel, or to any agent that retains moisture. Examples of a gel forming agents include, but are not limited to, food starches (e.g., potato starch, rice starch and corn starch) modified starches (e.g., sodium starch glycolate, modified potato starch, modified rice starch and modified corn starch) and bovine collagen peptides.

It has been found that the combination of a bovine gelatin and a fish gelatin provides an excellent mouth feel, i.e., it provides a pleasing sensory interaction with the mouth based on initial perception on the palate and through mastication. Although bloom values are relevant, and while not being bound by any particular theory, it is believed that the unique characteristics of the gelatin source, more particularly the interaction of bovine gelatin and fish gelatin, contribute to the superior mouth feel of the present chewable gelatin formulations beyond which can be attributed to proper selection of bloom values alone. Bovine source gelatin of the same bloom count is comparatively more rigid, which means it is more chewy as a finished product. While fish gelatin, even of the same bloom count, is more elastic and combines with the bovine gelatin to provide greater mouth feel. The fish gelatin requires lower gelling temperature and it melts faster as compared to the bovine source.

In one embodiment, the weight ratio of bovine gelatin:fish gelatin is from about 0.5 to about 7.5. In one embodiment the weight ratio of bovine gelatin:fish gelatin is from about 0.5 to about 5.0, or from about 1.7 to about 3.1 (e.g., 2.9). In one embodiment, the amount of bovine gelatin, prior to drying, ranges from about 15% to about 32%, or from about 18% to about 20%. In one embodiment the amount of fish gelatin, prior to drying, ranges from about 4% to about 14%, or from about 5% to about 10%, or from about 6% to about 7%. Post-drying, the above amounts of bovine gelatin and fish gelatin can be increased by 30-40% (e.g., 34%), due to the loss of water during the drying process.

In one embodiment, sodium starch glycolate is absent from the formulation. In one embodiment, sodium starch glycolate is at least substantially absent from the formulation. In one embodiment, the amount of sodium starch glycolate is from 0.4% to 0.0%, by weight of the formulation.

In one embodiment, hydrogenated vegetable oil is absent from the formulation. In one embodiment, hydrogenated vegetable oil is at least substantially absent from the formulation. In one embodiment, the amount of hydrogenated vegetable oil is from 0.05% to 0.0%, by weight of the formulation.

In one embodiment, bovine/porcine source collagen peptide is absent from the formulation. In one embodiment, bovine collagen peptide is at least substantially absent from the formulation. In one embodiment, the amount of bovine collagen peptide is from 6% to 15.0%, by weight of the formulation.

Certain embodiments of the present application can also be described without regard to the source of the gelatin. Accordingly, one embodiment of the present application provides a chewable gelatin formulation, as applied to the encapsulating machine and prior to drying, that includes from about 15% to about 32% of a low bloom gelatin (e.g., about 19%), from about 3.5% to about 13.0% of a high bloom gelatin, (e.g., about 6.5%) from about 20.0% to about 35% of a plasticizer, such as glycerin (e.g., about 27.1%), from about 20 to about 40% of water (e.g., about 30.3%); from about 8.0% to about 35.0% of a gel forming agent, such as modified potato starch (e.g., about 16.0%) and/or bovine collagen peptide (e.g., about 10%), from about 0.2% to about 1.5% of an anti-tacking and softening agent, such as sunflower lecithin (e.g. about 0.7%), less than 5% of a flavorant, such as flavorants selected from one or more of vanillin, lemon oil, citric acid and natural and artificial flavors, optionally, less than 2% of a sweetener, such as sucralose, optionally, less than 5% of a colorant and less than 2% of a natural preservative, like citric acid, potassium sorbate, rosemary extract and alpha tocopherol (e.g. about 1.25%).

In one embodiment, the flavorant is selected from citric acid, natural flavors and artificial flavors. In one embodiment, citric acid is incorporated and serves as both a flavorant and a preservative, and the sole preservative in the formulation is citric acid. In one embodiment, lemon oil is excluded as a flavorant. In one embodiment the preservative is selected from one or more of potassium sorbate, rosemary extract and alpha tocopherol. In one embodiment the preservative is selected from one or more of citric acid, potassium sorbate, rosemary extract and alpha tocopherol. In one embodiment, both bovine collagen peptides and a modified potato starch are incorporated.

Besides bovine gelatin, porcine gelatin can be used as a replacement for, or as a supplement to, bovine gelatin as the low bloom gelatin in certain alternative and non-limiting embodiments.

In one embodiment, the weight ratio of low bloom gelatin: high bloom gelatin is from about 1.0 to about 3.5. In one embodiment the weight ratio of low bloom gelatin:high bloom gelatin is from about 1.5 to about 3.2, or from about 1.7 to about 3.1. In one embodiment, the amount of low bloom gelatin, prior to drying, ranges from about 16.5% to about 25%, or from about 18% to about 20%. In one embodiment the amount of high bloom gelatin, prior to drying, ranges from about 4% to about 14%, or from about 5% to about 10%, or from about 6% to about 7%. Post-drying, the above amounts of bovine gelatin and fish gelatin are each increased by, for example, 30-40% (e.g., 34%), due to the loss of water during the drying process, but weight ratios of gelatin components should not be affected.

The chewable gelatin formulations of the present application can be prepared according to conventional methods. For example, they can be produced a rotary die process in which a molten mass of a gelatin sheath formulation is fed from a reservoir onto drums to form two spaced sheets or ribbons of gelatin in a semi-molten state. These ribbons are fed around rollers and brought together at a convergent angle into the nip of a pair of roller dies that include opposed die cavities. A liquid or paste containing the therapeutically active agent or other material to be encapsulated is fed into the wedge-shaped joiner of the ribbons.

The gelatin ribbons can be continuously conveyed between the dies, with the active agent being trapped between the sheets inside the die cavities. The sheets can then be pressed together, and severed around each die so that opposed edges of the sheets flow together to form a continuous gelatin sheath around the entrapped active agent. Alternatively, the active agent can be incorporated into the gelatin sheaths. The part of the gelatin sheet that is severed from the segments forming the capsules can be collected for recycling. The very soft capsules can then be dried to increase the integrity of the sheath, and packaged for later distribution and consumption.

EXAMPLES

Example 1

Dispense the required quantity of raw materials and transfer them to the gel preparation room. Heat the jacketed melter up to 60-65° C. and maintain the temperature range. Transfer weighed quantity of purified water (6.65 kg out of total 15.15 kg for 50 kg colored gelatin solution) and turn on the agitator. Let the melter attain the temperature of 60°-65° C.

Pour remaining quantity of purified water (8.5 kg out of total 15.15 kg for 50 kg colored gelatin solution) in a clean SS vessel and suspend the given quantity of food starch by rigorous manual mixing.

Add 0.500 kg out of the given quantity of glycerin and heat it to 60°-65° C. using a hot-plate. Dissolve the weighed quantity of vanillin in it. Turn off the heater.

Transfer the remaining quantity of glycerin to the jacketed melter containing purified water and let it attain the temperature of 60-65° C. Once the temperature is achieved transfer the weighed quantity of bovine gelatin, 150 bloom (Gelita) and fish gelatin, 275 bloom (Rousselot) simultaneously in to the melter containing purified water and glycerin mixture. Let the mixture mix in the melter for 10 minutes.

Afterwards, transfer the food starch solution, that was prepared earlier, in to the melter when it has achieved the temperature of 60-65° C. and mix it for 15 minutes. Also add the vanillin-glycerin solution prepared earlier in to the melter. If any colorant or a flavorant is to be added, it is added at this step by dissolving the solid parts of colorant into the minimum approximated quantity of purified water.

Following that step, ensure that the lid of the melter is properly closed. Turn on the vacuum and control the foam by opening and closing the vent valve until the foam is stabilized in the melter.

Continue the de-aeration process under vacuum for 65-80 minutes.

Turn off the agitator and turn off the vacuum. Check the viscosity by taking the sample of gelatin solution from the bottom valve of the melter. Viscosity should be within the optimum range as specified between, 5,000-20,000 CPS. If viscosity is within the range, continue unloading the gelatin solution in a clean SS jacketed gelatin holding tank (with the ancillary facilities of regulating pressure and maintaining temperature in the tank). If viscosity is higher than the limit specified add 2-4 kg of purified water and continue the agitation under vacuum for 15 minutes. If viscosity is lower than the limit specified, continue agitation under vacuum for 15-20 minutes or until it falls within the desired range.

During the storage the temperature of the gelatin solution should be maintained at 55±5° C.

The quantity of water to be added during gelatin preparation further includes an extra amount to compensate the loss due to evaporation during de-aeration. The amount added can vary within the range of 25-40%.

Encapsulation Procedure

The required fill material which can contain a therapeutically active agent is prepared and held in a fill material tank. The tank containing gelatin solution and the fill material tank are placed in close proximity to a die roll encapsulation machine (Arbes Cap-X-S). Weight percentages referenced in Examples 1 and 2 refer to the gelatin solution as it is initially fed to the encapsulation machine.

The die roll sizes varying from 3 MIN SQUARE to 24 MIN SQUARE is used depending upon the required filling weight per unit dosage. Each die roll has a respective wedge that regulates the quantity of fill material periodically into the die cavities. The encapsulation machine speed is monitored between 1-4 RPM (rotations per minute). The gelatin solution tank is connected with the spreader boxes through plastic hoses. The spreader boxes are responsible to spread gelatin solution in the form of a ribbon on the cooling drum with a clean oil-free surface. The gelatin tank is maintained at 55°±5° C. The spreader boxes' temperature is maintained within the range of 110°-140° F. The wedge temperature is in the range of 90°-115° F. The cooling drum's air flow is monitored within temperature range of 57°-64° F. The ribbon thickness is maintained at an average of 34 Thou with the limits stated 30-36 Thou. The seal thickness of the gel melt must not be less than 0.008 inches.

Figure 1:
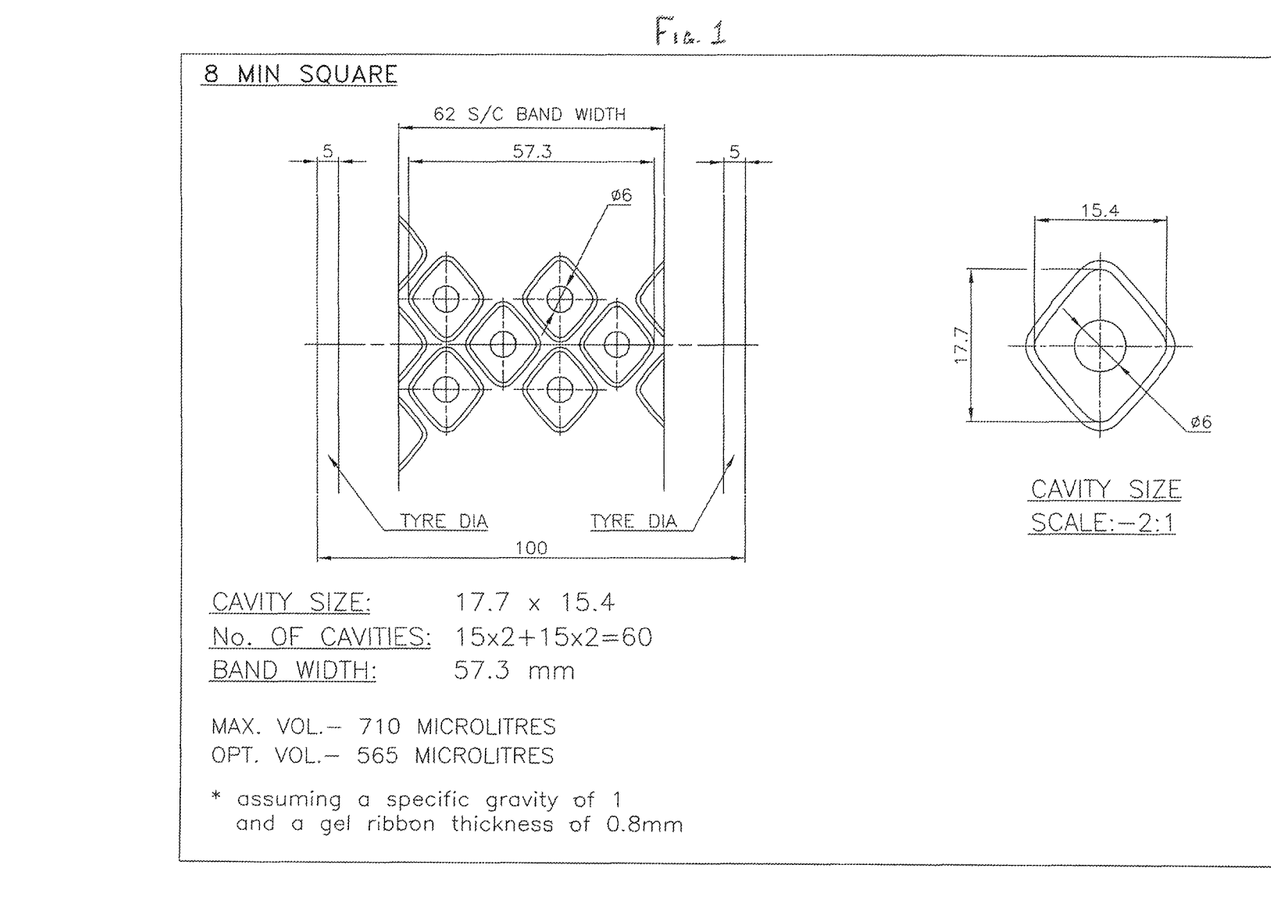
FIG. 1 depicts 8 min square encapsulation die rolls that can be used to prepare chewable gelatin formulations, as described in Example 1.
Figure 2:
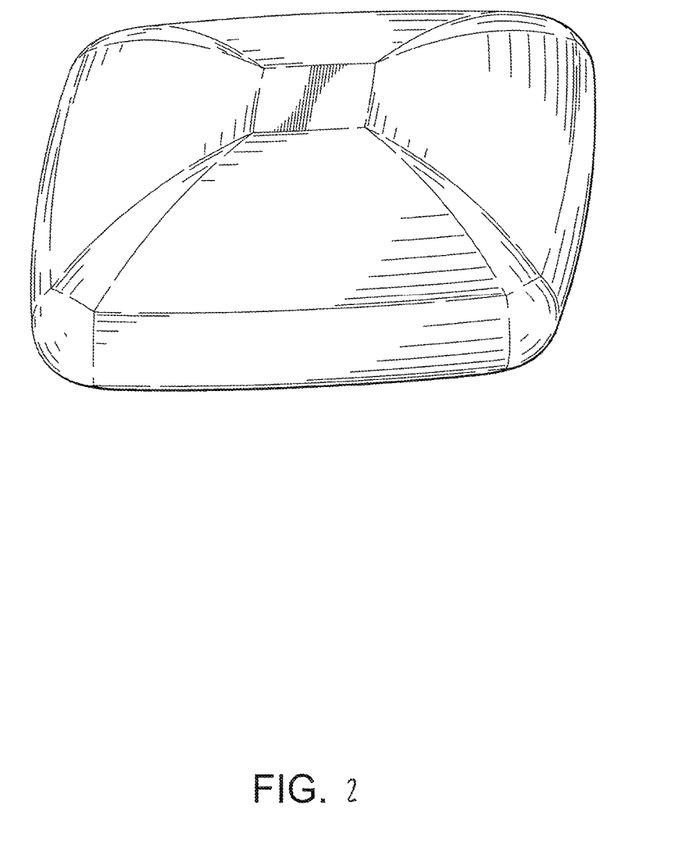
FIG. 2 depicts a chewable gelatin formulation according one non-limiting embodiment of the present application.
Figure 3:
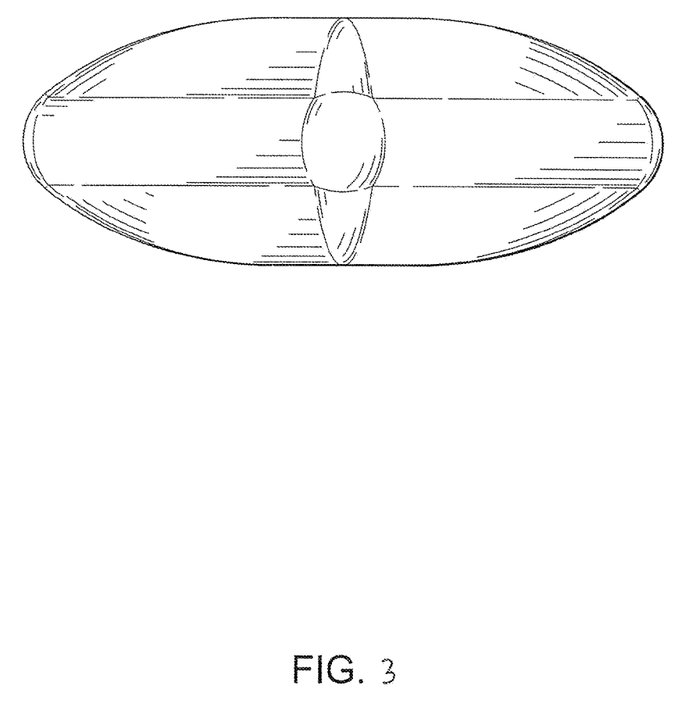
FIG. 3 depicts an alternative view of the gelatin formulation also depicted in FIG. 2.
Figure 4:
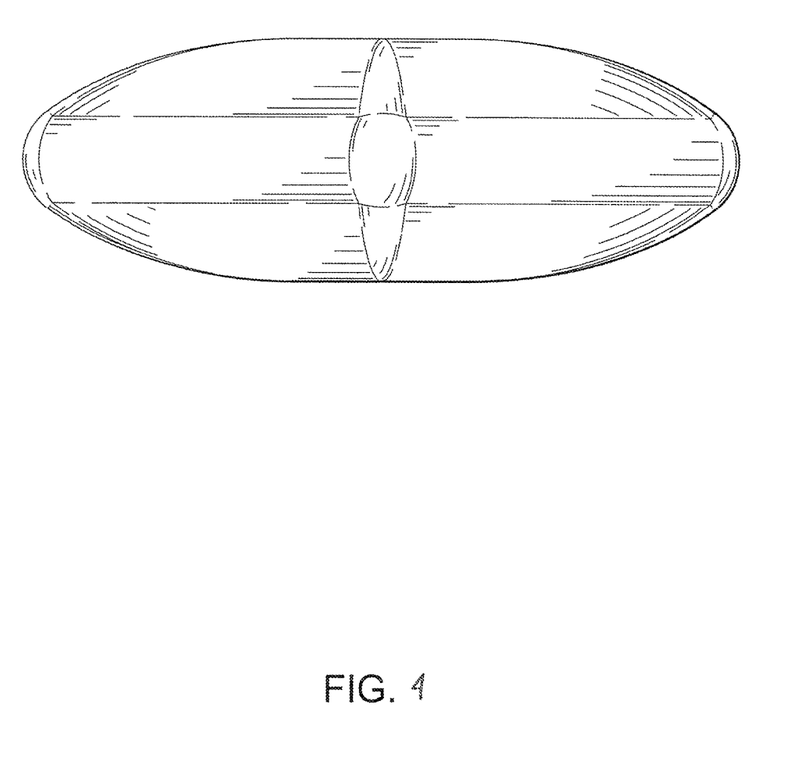
FIG. 4 depicts an alternative view of the gelatin formulation also depicted in FIG. 2.
Figure 5:
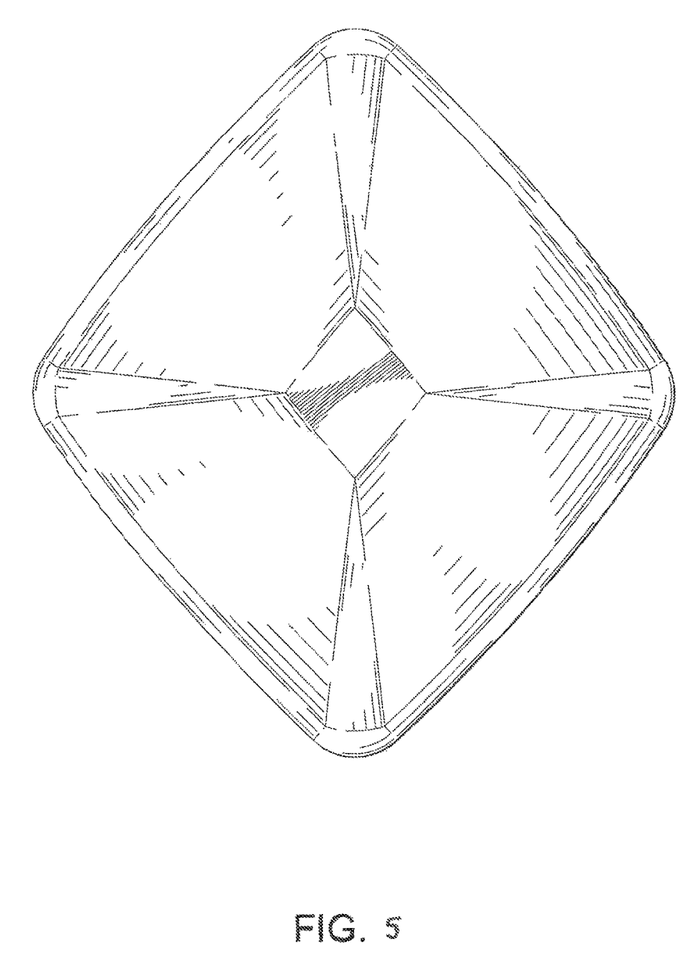
FIG. 5 depicts an alternative view of the gelatin formulation also depicted in FIG. 2.

An initial step is to encapsulate placebo with light mineral oil or PEG 400 or medium chain triglycerides in order to adjust the injection pump for the initial weight setting. Once the desired weight is achieved, the placebo gel melts are removed from the chute and the conveyor belt and are disposed. Light mineral oil is removed from the hopper and the hopper is cleaned. Afterwards, the encapsulation machine is set using fill material to the desired fill weight. Once the desired fill weight is achieved, encapsulation machine is continuously monitored for fill weight, ribbon thickness, wedge temperature, spreader box temperature at every hour and seal thickness of the gel melts is monitored at about every three hours to be within limits. 8 min square encapsulation die rolls are depicted in FIG. 1, although sizes of 3 min to 24 min square could also be used.

The formulated gel melts are allowed to pass into the tumble dryer at room temperature and are allowed to dry for about 2 hours. The final product that is received on the other end of the tumble dryers is collected and spread on the trays. The trays are moved to the drying units. The gel melts are further dried under the temperature of 65°–80° F. and humidity of 18-30% RH.

The gel melts are removed from the trays having a hardness that can vary from 25-150 grams such that the average hardness is from 50-200 grams, as measured on a calibrated Texture Analyzer. The gel melts are removed in transparent plastic bags and are further polished in the polishing pan using three polishing clothes for each bag containing gel melts. The polished gel melts are transferred to the packaging machine for further packaging. Based on the above process, the following formulations were prepared, with the amounts shown below representing the gelatin solution fed to the encapsulation machine.

[Formulation 27]

| Component | Amount (w/w) |
| --- | --- |
| bovine gelatin 150 bloom | 19 |
| fish gelatin 275 bloom | 6.5 |
| glycerin | 27.1 |
| water | 30.3 |
| modified potato starch (PenBind 100 ®) | 16 |
| sunflower lecithin | 0.7 |
| vanillin | 0.4 |
| natural and artificial flavors | as required |
| lemon oil | 0.025 |
| natural and artificial colors | as required |

[Formulation 28]

| Component | Amount (w/w) |
| --- | --- |
| bovine gelatin 150 bloom | 19 |
| fish gelatin 275 bloom | 6.5 |
| glycerin | 27.1 |
| water | 30.3 |
| modified potato starch (PenBind 100 ®) | 16 |
| sunflower lecithin | 0.7 |
| sucralose | 0.02 |
| vanillin | 0.4 |
| natural and artificial flavors | as required |
| lemon oil | 0.025 |
| natural and artificial colors | as required |

After drying, non-water component amounts of the chewable gelatin formulation can each increase by 30-40% (e.g., about 34%), and the water can be reduced by about 70-90% (e.g., about 77%) depending on drying time and conditions.

Example 2

By a similar procedure as described in Example 1, gelatin formulations were prepared based on the gelatin solution fed to the encapsulation machine having the following compositions:

[Formulation 1]

| Component | Amount (w/w) |
| --- | --- |
| bovine gelatin 150 bloom | 36 |
| glycerin | 27 |
| water | 36.2 |
| hydrogenated vegetable oil (Sterotex ®) | 0.7 |
| natural and artificial flavors | as required |
| lemon oil | 0.1 |
| natural and artificial colors | as required |

Hydrogenated vegetable oil (HVO) was employed a softening agent using 150 bloom bovine gelatin and glycerin as plasticizer. Soft and easy to chew gels were expected, but it was noted that mouth feel and chewability could be improved.

[Formulation 2]

| Component | Amount (w/w) |
| --- | --- |
| bovine gelatin 150 bloom | 38 |
| glycerin | 27 |
| water | 33.82 |
| hydrogenated vegetable oil (Sterotex ®) | 1 |
| natural and artificial flavors | as required |
| lemon oil | 0.18 |
| natural and artificial colors | as required |

Additional HVO was added with the same quantity of 150 bloom bovine gelatin and glycerin as plasticizer. Gels were difficult to chew and unacceptable mouth feel was observed.

[Formulation 3]

| Component | Amount (w/w) |
| --- | --- |
| bovine gelatin 150 bloom | 36 |
| glycerin | 30 |
| water | 32.4 |
| hydrogenated vegetable oil (Sterotex ®) | 0.6 |
| natural and artificial flavors | as required |
| lemon oil | 1.0 |
| natural and artificial colors | as required |

Replacements for HVO were considered. Additional plasticizer was added to make shell more flexible. But the resulting gels were harder and chewier than desired.

[Formulation 4]

| Component | Amount (w/w) |
| --- | --- |
| bovine gelatin 150 bloom | 28 |
| glycerin | 30 |
| water | 40.9 |
| hydrogenated vegetable oil (Sterotex ®) | 1.0 |
| natural and artificial flavors | as required |
| lemon oil | 0.1 |
| natural and artificial colors | as required |

Bovine gelatin 150 bloom quantity was reduced by almost 22% keeping the quantity of HVO the same as in Formulation 2 to see if gelatin is causing gels to be hard. Gels were as hard as in prior experiments and also exhibited leaks the very next day in spite of storing it below normal room temperature.

[Formulation 5]

| Component | Amount (w/w) |
| --- | --- |
| bovine gelatin 150 bloom | 36 |
| glycerin | 30 |

-continued

| Component | Amount (w/w) |
| --- | --- |
| water | 29 |
| modified potato starch (PenBind 100 ®) | 4 |
| hydrogenated vegetable oil (Sterotex ®) | 0.2 |
| cellulose | 0.6 |
| sucralose | 0.1 |
| natural and artificial flavors | as required |
| lemon oil | 0.1 |
| natural and artificial colors | as required |

From the variety of starches available in the market, PenBind 100® was selected do to its excellent gel forming capacity and stability over time.

Potato starch molecules have a larger semi-crystalline granular size that swells in the presence of water and burst forming a network of amylose and the mixture that holds water as well as improves the viscosity of the mixture. Hence it was added to the formulation, dissolved in water and in conjunction with cellulose, as a mild moisture retaining agent and a mild thickener, to develop the cross-linked gel structure between bovine gelatin and plasticizer. In the same experiment HVO was reduced back to 0.2% to confirm the effect of starch in the formulation. Gels were not very hard but not optimal, and it also leaked after 10 days from encapsulation.

[Formulation 6]

| Component | Amount (w/w) |
| --- | --- |
| bovine gelatin 150 bloom | 28 |
| glycerin | 30 |
| water | 32.64 |
| modified potato starch (PenBind 100 ®) | 8 |
| hydrogenated vegetable oil (Sterotex ®) | 0.1 |
| cellulose | 1.0 |
| sucralose | 0.1 |
| natural and artificial flavors | as required |
| lemon oil | 0.16 |
| natural and artificial colors | as required |

Data from the previous experiment led to doubling the amount of PenBind 100® starch with the expectation of improving the gel formation preventing the leakers and also restrain its chewability with better mouth feel. And again gelatin quantity was brought down by 22% to observe the effect of starch and to confirm if excessive gelatin is what making the formulation chewier. The cellulose was increased to promote the moisture retaining capacity of the shell. Gels were soft but leaked the next day in the storage room at normal storage conditions. This indicated the improper cross-links in the gel structure of the shell.

[Formulation 7]

| Component | Amount (w/w) |
| --- | --- |
| bovine gelatin 150 bloom | 32 |
| glycerin | 28 |
| maltitol (Maltidex ™) | 2 |
| water | 34.3 |
| modified potato starch (PenBind 100 ®) | 3 |
| sodium starch glycolate | 0.5 |
| sucralose | 0.1 |
| natural and artificial flavors | as required |
| lemon oil | 0.1 |
| natural and artificial colors | as required |

Afterwards, as per the results from prior experiment, further 3 experiments were carried out using maltitol (Maltidex™) in the ranges of 2-4% as an additional plasticizer along with glycerin. Starch added was in the range of 1-9% along with modified starch as sodium starch glycolate (SSG) in the range of 0.2-3%. The starches were blended to understand their effect on the gel structure. The gels were soft but had an unacceptable mouth feel. Also leaks were observed after a period of one month.

[Formulation 8]

| Component | Amount (w/w) |
| --- | --- |
| bovine gelatin 150 bloom | 32 |
| glycerin | 28 |
| maltitol (Maltidex ™) | 2 |
| water | 28.6 |
| modified potato starch (PenBind 100 ®) | 9 |
| sodium starch glycolate | 0.2 |
| sucralose | 0.09 |
| natural and artificial flavors | as required |
| lemon oil | 0.1 |
| natural and artificial colors | as required |

[Formulation 9]

| Component | Amount (w/w) |
| --- | --- |
| bovine gelatin 150 bloom | 34 |
| glycerin | 24 |
| maltitol (Maltidex ™) | 4 |
| water | 33.8 |
| modified potato starch (PenBind 100 ®) | 1 |
| sodium starch glycolate | 3 |
| sucralose | 0.1 |
| natural and artificial flavors | as required |
| lemon oil | 0.1 |
| natural and artificial colors | as required |

[Formulation 10]

| Component | Amount (w/w) |
| --- | --- |
| bovine gelatin 150 bloom | 28 |
| glycerin | 26 |
| maltitol (Maltidex ™) | 1 |
| water | 30.8 |
| modified potato starch (PenBind 100 ®) | 14 |
| sucralose | 0.1 |
| natural and artificial flavors | as required |
| lemon oil | 0.1 |
| natural and artificial colors | as required |

SSG was not used in this experiment as it was observed in the prior art that it has no effect on the gel structure and the gels were found to leak over time. The concentration of potato starch was increased to 14% in the formulation. The gelatin and glycerin concentration were relatively reduced to understand the reason for leaking issues. The gels resulted were soft and easily chewed with a slightly better mouth feel but again the gels leaked over the period of one month.

[Formulation 11]

| Component | Amount (w/w) |
| --- | --- |
| bovine gelatin 150 bloom | 20 |
| glycerin | 18 |
| water | 39.9 |
| modified potato starch (PenBind 100 ®) | 22 |

These experiments were conducted with varying concentrations of PenBind 100® in the range of 21-22%. Also for all the experiments gelatin 150 bloom and glycerin were adjusted to observe the effect of starch with different concentrations of gelatin 150 bloom and glycerin. Gels were not as soft as expected and had leaking issues the next day in the storage room under standard conditions.

[Formulation 12]

| Component | Amount (w/w) |
| --- | --- |
| bovine gelatin 150 bloom | 18 |
| glycerin | 26 |
| water | 35.9 |
| modified potato starch (PenBind 100 ®) | 22 |
| natural and artificial flavors | as required |
| lemon oil | 0.1 |
| natural and artificial colors | as required |

[Formulation 13]

| Component | Amount (w/w) |
| --- | --- |
| bovine gelatin 150 bloom | 23 |
| glycerin | 22 |
| water | 32.9 |
| modified potato starch (PenBind 100 ®) | 22 |
| natural and artificial flavors | as required |
| lemon oil | 0.1 |
| natural and artificial colors | as required |

[Formulation 14]

| Component | Amount (w/w) |
| --- | --- |
| bovine gelatin 150 bloom | 21 |
| glycerin | 20 |
| water | 37.9 |
| modified potato starch (PenBind 100 ®) | 21 |
| natural and artificial flavors | as required |
| lemon oil | 0.1 |
| natural and artificial colors | as required |

[Formulation 15]

| Component | Amount (w/w) |
| --- | --- |
| bovine gelatin 150 bloom | 19 |
| glycerin | 24 |
| water | 33.4 |
| modified potato starch (PenBind 100 ®) | 23 |
| sodium starch glycolate | 0.5 |
| natural and artificial flavors | as required |
| lemon oil | 0.1 |
| natural and artificial colors | as required |

This trial was carried out with 23% of PenBind 100® along with 0.5% of SSG to improve the cross-link structure between glycerin and gelatin, which ultimately renders more strength to the gelatin shell for longer period. Gels were soft but very sticky and still leaked after few hours of encapsulation.

[Formulation 16]

| Component | Amount (w/w) |
| --- | --- |
| bovine gelatin 150 bloom | 22 |
| fish gelatin 275 bloom | 0.5 |
| glycerin | 24.7 |
| water | 31.68 |
| modified potato starch (PenBind 100 ®) | 21 |
| sodium starch glycolate | 0.05 |
| xylitol | 0.05 |
| natural and artificial flavors | as required |
| lemon oil | 0.025 |
| natural and artificial colors | as required |

At this stage gelatin 150 bloom from bovine was combined with 275 bloom fish gelatin (0.5%) to render more elasticity to the gelatin shell. Bovine gelatin is more fragile and it was believed to be the source of the leakage issues. In order to improve the elasticity fish gelatin of 275 bloom was incorporated in the experiment. Also starch concentration was brought down to 20-21% as compared to previous experiments. A 0.05% portion of SSG was added along with 0.05% of xylitol to enhance the palatability of the shell. Gels were not very hard but still leaked after 2 days of encapsulation under standard storage conditions.

[Formulation 17]

| Component | Amount (w/w) |
| --- | --- |
| bovine gelatin 150 bloom | 23 |
| fish gelatin 275 bloom | 0.5 |
| glycerin | 24.7 |
| water | 31.68 |
| modified potato starch (PenBind 100 ®) | 20 |
| sodium starch glycolate | 0.05 |
| xylitol | 0.05 |
| natural and artificial flavors | as required |
| lemon oil | 0.025 |
| natural and artificial colors | as required |

[Formulation 18]

| Component | Amount (w/w) |
| --- | --- |
| bovine gelatin 150 bloom | 23.5 |
| fish gelatin 275 bloom | 0.5 |
| glycerin | 26 |
| water | 30.18 |
| modified potato starch (PenBind 100 ®) | 19 |
| sunflower lecithin | 0.8 |
| natural and artificial flavors | as required |
| lemon oil | 0.025 |
| natural and artificial colors | as required |

Prior experiments indicated that SSG was not making any difference in the gel forming structure as it was expected to enhance the binding stability. Surprisingly, it was found that under the circumstances tested, SSG acted as a disintegrant and so it was not used in this experiment. Bovine Gelatin 150 bloom was combined with Fish gelatin 275 bloom at the concentrations of 23.5% and 0.5% respectively. The concentration of PenBind 100® used here was 19%. An anti-tacking and a softening agent, sunflower lecithin, was added in the formulation which also served as a partial emulsifier. Because an anti-tacking agent was added to prevent the sticking of gels together, concentration of starch was reduced to 19%.

[Formulation 19]

| Component | Amount (w/w) |
| --- | --- |
| bovine gelatin 150 bloom | 23.5 |
| fish gelatin 275 bloom | 0.5 |
| glycerin | 26 |
| water | 30.98 |
| modified potato starch (PenBind 100 ®) | 19 |
| natural and artificial flavors | as required |
| lemon oil | 0.025 |
| natural and artificial colors | as required |

The experiment was conducted with the same concentration of ingredients as above except sunflower lecithin. This experiment was conducted to justify the effect of sunflower lecithin as an anti-tacking agent.

The gels from formulation 18 were hard and lacked chewability. Gels were not sticky at all. And leaking issues were observed after five hours of encapsulation.

The gels from formulation 19 were hard, lacked chewability and moderately leaking after five hours of encapsulation.

[Formulation 20]

| Component | Amount (w/w) |
| --- | --- |
| bovine gelatin 150 bloom | 25 |
| fish gelatin 275 bloom | 0.5 |
| glycerin | 27.5 |
| water | 30.28 |
| modified potato starch (PenBind 100 ®) | 16 |
| sunflower lecithin | 0.7 |
| natural and artificial flavors | as required |
| lemon oil | 0.025 |
| natural and artificial colors | as required |

Gelatin 150 bloom was increased to 25% and glycerin was increased up to 27.5% to improve gel-stability. PenBind 100® was reduced to 16% to determine if it allowed the gels to be more hard and chewy. Sunflower lecithin was added as an anti-tacking and softening agent. Gels were soft with better chewability. But it leaked over the period of 5 days under standard storage conditions.

[Formulation 21]

| Component | Amount (w/w) |
| --- | --- |
| bovine gelatin 150 bloom | 25 |
| fish gelatin 275 bloom | 0.5 |
| glycerin | 28.5 |
| water | 29.98 |
| modified potato starch (PenBind 100 ®) | 16 |
| natural and artificial flavors | as required |
| lemon oil | 0.025 |
| natural and artificial colors | as required |

Glycerin was increased to 28.5% to render more plasticity to the gels. Another reason to increase the concentration of glycerin was to determine if it has the same effect that sunflower lecithin exerts on the gels. So in this experiment sunflower lecithin was not used. Gels were not soft and lacked chewability. Also the gels leaked after 3 hours of encapsulation under normal storage conditions.

[Formulation 22]

| Component | Amount (w/w) |
| --- | --- |
| bovine gelatin 150 bloom | 25 |
| fish gelatin 275 bloom | 0.5 |
| glycerin | 28 |
| water | 28.78 |
| modified potato starch (PenBind 100 ®) | 17 |
| sunflower lecithin | 0.7 |
| natural and artificial flavors | as required |
| lemon oil | 0.025 |
| natural and artificial colors | as required |

[Formulation 23]

| Component | Amount (w/w) |
| --- | --- |
| bovine gelatin 150 bloom | 25 |
| fish gelatin 275 bloom | 0.5 |
| glycerin | 28.5 |
| water | 28.98 |
| modified potato starch (PenBind 100 ®) | 17 |
| natural and artificial flavors | as required |
| lemon oil | 0.025 |
| natural and artificial colors | as required |

This time glycerin concentration was kept the same at 28-28.5% and starch was increased to 17% to see if stable gel formation is achieved. In both the experiments gels produced were tacky, not hard but were chewy and lacked mouth feel.

[Formulation 24]

| Component | Amount (w/w) |
| --- | --- |
| bovine gelatin 150 bloom | 12.65 |
| fish gelatin 275 bloom | 12.6 |
| glycerin | 27.7 |
| water | 30.3 |
| modified potato starch (PenBind 100 ®) | 16 |
| sunflower lecithin | 0.7 |
| natural and artificial flavors | as required |
| lemon oil | 0.025 |
| natural and artificial colors | as required |

This experiment was conducted with 12.65% of bovine gelatin medium bloom and 12.6% of fish gelatin 275 bloom. Starch was used at 16% and sunflower lecithin at 0.7%. Gels were very sticky and very soft. An improved mouth feel was observed and it did not leak under standard and accelerated storage conditions for a period of two months. Minor leaks were observed after two months. Moreover, gels were very sticky.

Having performed satisfactorily, formulation 24 was taken as leading candidate and additional improvement was sought based on this formulation.

[Formulation 25]

| Component | Amount (w/w) |
| --- | --- |
| bovine gelatin 150 bloom | 19 |
| fish gelatin 240 bloom | 6.5 |
| glycerin | 27.5 |
| water | 30.3 |
| modified potato starch (PenBind 100 ®) | 16 |
| sunflower lecithin | 0.7 |

-continued

| Component | Amount (w/w) |
|---|---|
| natural and artificial flavors | as required |
| lemon oil | 0.025 |
| natural and artificial colors | as required |

One trial was attempted using bovine gelatin 150 bloom in combination with fish gelatin 240 bloom, a different bloom strength. Gels were soft but tacky and leaked over time.

[Formulation 26]

| Component | Amount (w/w) |
|---|---|
| bovine gelatin 150 bloom | 16.5 |
| fish gelatin 240 bloom | 9.0 |
| glycerin | 27.5 |
| water | 30.3 |
| modified potato starch (PenBind 100 ®) | 16 |
| sunflower lecithin | 0.7 |
| natural and artificial flavors | as required |
| lemon oil | 0.025 |
| natural and artificial colors | as required |

Another trial was conducted using bovine gelatin 150 bloom in adjunction with fish gelatin 240 bloom. Gels leaked over the period.

[Formulation 27]

| Component | Amount (w/w) |
|---|---|
| bovine gelatin 150 bloom | 19 |
| fish gelatin 275 bloom | 6.5 |
| glycerin | 27.1 |
| water | 30.3 |
| modified potato starch (PenBind 100 ®) | 16 |
| sunflower lecithin | 0.7 |
| vanillin | 0.4 |
| natural and artificial flavors | as required |
| lemon oil | 0.025 |
| natural and artificial colors | as required |

[Formulation 28]

| Component | Amount (w/w) |
|---|---|
| bovine gelatin 150 bloom | 19 |
| fish gelatin 275 bloom | 6.5 |
| glycerin | 27.1 |
| water | 30.3 |
| modified potato starch (PenBind 100 ®) | 16 |
| sunflower lecithin | 0.7 |
| sucralose | 0.02 |
| vanillin | 0.4 |
| natural and artificial flavors | as required |
| lemon oil | 0.025 |
| natural and artificial colors | as required |

With all those trial conducted previously, experiment 24 was observed as a stable trial. So the formula number 24 was taken and little changes were made based on the results. The high amount of fish gelatin 275 bloom was found responsible for the excessive tackiness in the gels. So fish gelatin 275 bloom's concentration was reduced down to 6.5%. Moreover, starch (gel-forming agent) and glycerin (plasticizer), being mild softeners were found to exert extra softness to the gels along with sunflower lecithin. So to counter the effect of excessive softness, gelatin 150 bloom was increased up to 19% that renders durability to the shell. Vanillin was added in the formulation as a flavorant. The results were impressive where the gels had an excellent mouth feel. The shells are intact up to date. No leakers were observed under standard storage conditions and accelerated conditions. Gels were not tacky and were soft enough to melt in the mouth.

Formulation 28: The formula is same as formula in 27 except it has a sucralose as a sweetener to improve palatability. Results obtained were similar to formulation 27 results.

Leaking gels or overly chewy gels have presented issues. Fish gelatin of higher bloom strength renders elasticity and bovine source of gelatin renders rigidity to the gel. Therefore, blending fish and bovine sources of gelatin was attempted in different concentrations. 0.5% of fish source of gelatin was used (in the blend with bovine source) in previous trials and it was also experimented using 12.6% of the same gelatin in the blend in one of the trials. Based on the results obtained in previous experiments a range of 0.5%-12.6% of fish gelatin was framed along with bovine source. Then in the progression, in one trial we experimented with 6.5% of fish source along with 19% of bovine source, 16% food starch, 0.7% sunflower lecithin, and additives (flavorants/colorants).

In the final formula food starch was used at the concentration of 16% which is comparatively at a low value as compared to previous experiments. Starch was included in the formulation for its gel-forming ability and it also renders stability to the cross-linked gel structure of gelatin and glycerin mixture. Starch has various characteristics such as gel forming/stabilizing ability, moisture-retaining ability, disintegrant, etc. In our formulation excessive quantity of starch acts as a disintegrant which might cause deformation in the cross-links causing the gels to leak over the period. Hence food starch's concentration was brought down to 16% in the final formula.

The non-tackiness and softness was provided by 0.7% of sunflower lecithin. Red palm oil, beeswax, hydrogenated vegetable oil and various other compounds can be used as anti-tacking and softening agents. Also, glycerin is a mild softening agent, but 0.7% sunflower lecithin in adjunction with the stated concentrations of other ingredients confers required softness and better mouth-feel to the final finished product.

The results obtained with formulation 27 and 28 were promising as far as mouth feel and the taste is concerned. Also, there were no leaking gels in the finished product over a considerable period of 180 days (3 months).

In formulation 28, the results were promising for a period of 180 days at room temperature. After 180 days, gels became chewy and the flavor lost its masking effect. The taste was a little bitter too. Considering that, another trial "Formulation 29" was taken. Fish gelatin 275 bloom was increased by 2% by weight to make the formulation more soft and palatable. The modified starch grade of higher strength (PenBind® 1000 was incorporated in the formulation to render stronger gel binding capability to the shell. Citric acid was added as a flavorant and a preservative to maintain the integrity of the shell for a longer period. Lemon oil was removed from the formulation as it was observed as the cause of leakers due to its strong acidic content.

[Formulation 29]

| Component | Amount (w/w) |
| --- | --- |
| bovine gelatin 150 bloom | 19 |
| fish gelatin 275 bloom | 8.5 |
| glycerin | 27.1 |
| water | 30.45 |
| modified potato starch (PenBind 1000 ®) | 13 |
| sunflower lecithin | 0.7 |
| Citric acid | 1.25 |
| natural and artificial flavors | as required |
| natural and artificial colors | as required |

The results of the formulation 29 were positive. The softgel samples are in the second month of observation at room temperature. There was no leakage or deformities observed during the test period.

As mentioned earlier there was a considerable chewyness and leakage with the stability samples from formulation 28. Another trial along with formulation 29 was taken. In the formulation 30, a combination of modified food starch PenBind 100® and bovine source of collagen peptides was used as a gel binding agent to ensure the shell integrity in the formulation. In this trial, Penbind 100® was reduced to 8% and bovine collagen peptides were used at 10% by weight in the formulation. Gelatin 150 bloom was increased to 26% to improve the cross-linkage between gelatin and glycerin. Gelatin 275 bloom was kept at the same concentration of 9%.

[Formulation 30]

| Component | Amount (w/w) |
| --- | --- |
| bovine gelatin 150 bloom | 26 |
| fish gelatin 275 bloom | 9 |
| glycerin | 22 |
| water | 23.25 |
| modified potato starch (PenBind 100 ®) | 8 |
| Bovine Collagen peptides | 10 |
| sunflower lecithin | 0.5 |
| Citric acid | 1.25 |
| natural and artificial flavors | as required |
| natural and artificial colors | as required |

The outcome of this trial was very soft gels with little to no chewyness. Currently, the samples are under 3 month observation period under normal conditions of temperature.

After formulation trial 30, two more trials were considered to ensure the effect of collagen peptides as a gel binding agent.

[Formulation 31]

| Component | Amount (w/w) |
| --- | --- |
| bovine gelatin 150 bloom | 24 |
| fish gelatin 275 bloom | 9 |
| glycerin | 22 |
| water | 25.50 |
| modified potato starch (PenBind 100 ®) | 4 |
| Bovine Collagen peptides | 14 |
| sunflower lecithin | 0.5 |
| Citric acid | 1.25 |
| natural and artificial flavors | as required |
| natural and artificial colors | as required |

[Formulation 32]

| Component | Amount (w/w) |
| --- | --- |
| bovine gelatin 150 bloom | 26 |
| fish gelatin 275 bloom | 9 |
| glycerin | 22 |
| water | 25.25 |
| modified potato starch (PenBind 100 ®) | 13 |
| Bovine Collagen peptides | 6 |
| sunflower lecithin | 0.5 |
| Citric acid | 1.25 |
| natural and artificial flavors | as required |
| natural and artificial colors | as required |

The gels from the above two trials were not leaking and were stable at room temperature. And currently these samples are in the observation period at room temperature.

Example 3

The formulations were prepared and dried as generally described above in Example 1. Pre-dried amounts of gelatin feed solution and post-dried amounts of the as-prepared formulation (excluding fill material) are shown below, provided that the post-dried amounts do not include the use of any colorants, flavorants or sweetening agents:

| Component | Pre-Dried Amount (w/w) | Post-Dried Amount (w/w) |
| --- | --- | --- |
| bovine gelatin 150 bloom | 19 | 24.58 |
| fish gelatin 275 bloom | 6.5 | 8.41 |
| modified potato starch (PenBind 100 ®) | 16 | 20.70 |
| glycerin | 27.1 | 35.06 |
| sunflower lecithin | 0.7 | 0.91 |
| water | 30.7 | 10.35 |

The invention claimed is:
1. A gelatin sheath comprising:
   (a) from about 22% to about 34% of bovine gelatin having a bloom value of from about 125 to about 175;
   (b) from about 4.5% to about 18.0% of fish gelatin having a bloom value of from about 250 to about 300;
   (c) from about 26.0% to about 47% of glycerin;
   (d) from about 4.0% to about 10.0% of water;
   (e) from about 2.6% to about 28.5% of a modified potato starch;
   (f) from about 7.8% to about 35.0% of bovine collagen peptides;
   (g) from about 0.3% to about 7.0% of sunflower lecithin; and
   (h) from about 0.3% to about 5.0% of a flavorant selected from one or more of vanillin, lemon oil, citric acid and natural and artificial flavors.
2. The gelatin sheath of claim 1, wherein the average hardness of the gelatin sheath is from about 65-85 grams, as measured on a calibrated Texture Analyzer.
3. The gelatin sheath of claim 1, further comprising less than 2.0% of a sweetener selected from one or more of the group consisting of: xylitol, sucralose, aspartame, sucrose, glucose, high fructose corn syrup, acesulfame potassium, thaumatin, glycyrrhiza glabra, siraitia grosvenorii and stevia rabaudiana.
4. The gelatin sheath of claim 1, further comprising less than 5.0% of a colorant selected from natural and artificial colors.

5. A chewable gelatin formulation comprising the gelatin sheath of claim 1 and at least one therapeutically active agent, wherein said sheath encapsulates said at least one therapeutically active agent.

6. The chewable gelatin formulation of claim 5, wherein the therapeutically active agent is selected from the group consisting of a vitamin, essential oils, fish oil, an OTC active agent, herbal extracts and minerals.

7. The chewable gelatin formulation of claim 5, further comprising less than 2.0% of a sweetener selected from the group consisting of one or more of xylitol, sucralose, aspartame, sucrose, glucose, high fructose corn syrup, acesulfame potassium, thaumatin, glycyrrhiza glabra, siraitia grosvenorii and stevia rabaudiana.

8. The chewable gelatin formulation of claim 5, further comprising less than 5.0% of a colorant selected from natural and artificial colors.

* * * * *